United States Patent [19]
Batzle et al.

[11] Patent Number: 5,166,910
[45] Date of Patent: Nov. 24, 1992

[54] METHOD AND APPARATUS FOR MEASURING THE ACOUSTIC VELOCITY

[75] Inventors: Michael L. Batzle, Plano; Billy J. Smith, Richardson, both of Tex.

[73] Assignee: Atlantic Richfield Company, Los Angeles, Calif.

[21] Appl. No.: 776,127

[22] Filed: Oct. 15, 1991

[51] Int. Cl.5 .............................................. H04B 11/00
[52] U.S. Cl. ...................................... 367/191; 73/597
[58] Field of Search ................ 181/112, 123; 367/13, 367/27, 40, 47, 49, 50, 140; 73/597, 614, 628, 644, DIG. 1, 866.5

[56] References Cited

U.S. PATENT DOCUMENTS

| | | | |
|---|---|---|---|
| 3,019,637 | 2/1962 | Cook et al. | 73/628 |
| 3,312,934 | 4/1967 | Stripling et al. | 367/27 |
| 3,979,714 | 9/1976 | Zemanek, Jr. | 367/27 |
| 4,631,963 | 12/1986 | Sprunt et al. | 367/13 |

Primary Examiner—Brian S. Steinberger
Attorney, Agent, or Firm—Joseph E. Rogers

[57] ABSTRACT

A portable device for accurately measuring acoustic velocities in solids. This portable hand-held device (100) uses dual receiving transducer tips (110, 112) to allow differential measurement of acoustic velocity in a solid. A body having a handle uses a transmitting transducer tip (108) to transmit acoustic energy to a solid. The first receiving transducer tip (110) is used in conjunction with a second receiving transducer tip (112) mounted on the body a fixed distance from the first (110). The device (100) uses the differences in the time of arrival of the wavefront at the first and second transducers to calculate the acoustic velocity in a given solid. This differential measurement method reduces acoustic velocity measurement inaccuracies.

8 Claims, 2 Drawing Sheets

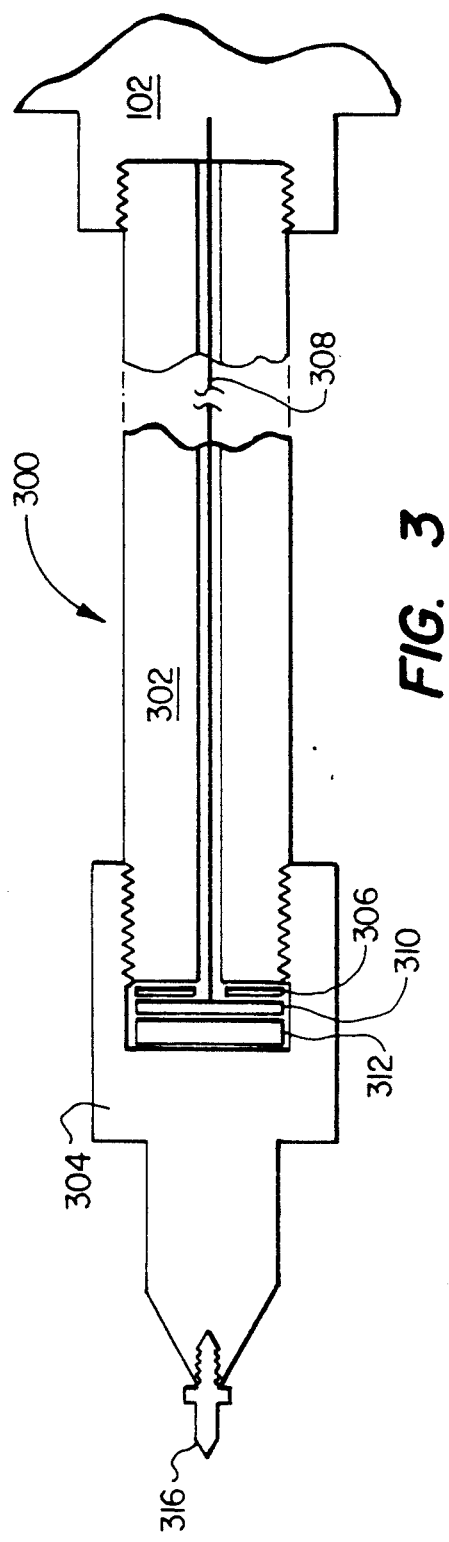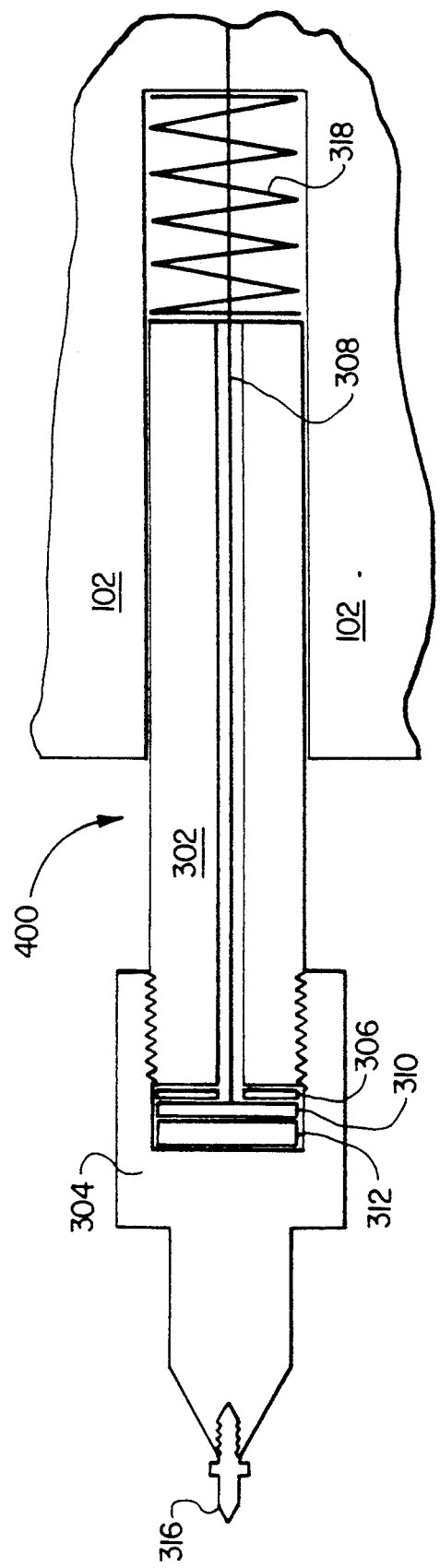

METHOD AND APPARATUS FOR MEASURING THE ACOUSTIC VELOCITY

FIELD OF THE INVENTION

This invention is related to the field of acoustic velocity measurement and is more particularly directed to measurement of acoustic velocities in rock samples, in situ measurement of acoustic velocities in outcrop, and rapid nondestructive testing of materials and structures at remote locations.

BACKGROUND OF THE INVENTION

Geologic study of the subsurface structure of the Earth continues to be an important field of endeavor. The continued search for producing reservoirs of hydrocarbons, such as oil and gas, is a particularly important motivation for conducting such studies and obtaining information concerning the Earth's subsurface structure.

One potential source of this information is the measurement of acoustic velocity in outcrops or rock samples. Changes in acoustic velocity can indicate regions of similar or dissimilar material and can also provide estimates of homogeneity and/or anistropy. Such information helps to predict the occurrence of hydrocarbon reservoir traps and provides information about the porosity of materials which is important for hydrocarbon production.

Acoustic velocity can also be helpful in correlating seismic data to well cores and can aid in fault detection. All of such information can lead to additional discoveries of hydrocarbons and to the increase in production from reservoirs. Thus, acoustic velocity information is an important piece of information in the exploration and production of hydrocarbons.

In addition, measurement of acoustic properties has proved useful in non-destructive materials testing applications such as fracture and flow detection, grain and lamination orientation determination, bond integrity evaluation, and material identification.

There are currently numerous hand-held or portable ultrasonic devices which are commercially available. Almost all of these existing devices are used for distance or thickness measurements and not velocity measurements. Ultrasonic thickness gauges are often used on pipes and other equipment and marine sonic systems are commonly used as depth sounders or fish finders. Some ultrasonic devices have been used to measure the flow rate or movement velocity of a liquid. In addition, sonic logs of boreholes have been useful in exploration and production of hydrocarbons.

More recently, acoustic velocity measurement of rock samples has been accomplished using hand-held apparatus. Such hand-held apparatus are known in the art and include a single source and single receiver transducer a fixed distance apart. The source transducer imparts acoustic energy into the sample. The resulting acoustic wave travels through the sample and, given the fixed distance between source and receiver, its velocity is calculated using the difference in time between transmission and arrival at the receiver. Unfortunately, the current systems are susceptible to poor coupling between the transmitting transducer and the rock sample and are also susceptible to errors caused by differences between the transmitted acoustic energy wave form and received wave form resulting from inherent properties of the rock sample. Much effort has been applied to developing an acoustic velocity measuring system which eliminates such potential errors.

SUMMARY OF THE INVENTION

According to the present invention, a device for measuring the velocity of sound in a solid is provided. The device comprises:

(a) a body having a handle;

(b) a pulse generator for producing an electrical pulse;

(c) a transmitting transducer assembly on the body and electrically connected to the pulse generator for converting the electrical pulse to acoustic signals and transmitting acoustic signals to the solid;

(d) a first receiving transducer assembly on the body displaced from the transmitting transducer assembly for receiving acoustic signals transmitted through the solid and converting acoustic signals to a first set of electrical pulses;

(e) a second receiving transducer on the body a fixed distance on a line formed by the transmitting transducer assembly and the first receiving transducer, further removed from the transmitting transducer assembly than is the first receiving transducer assembly for receiving acoustic signals transmitted through the solid and converting acoustic signals to a second set of electrical pulses; and (f) a waveform analysis unit electrically connected to the first and second transducer assemblies for determining the time difference between a time of arrival for the first set of electrical pulses and the second set of electrical pulses;

thereby enabling calculation of the velocity of sound through the fixed distance of the solid between the first and second receiving transducer assemblies.

According to the present invention a method for measuring acoustic velocity of a solid is provided. This method comprises:

(a) transmitting acoustic energy into the solid at a first point on the surface of the solid forming an acoustic wavefront;

(b) recording a first time of arrival for the acoustic wavefront energy at a second point on the surface of the solid;

(c) recording a second time of arrival for the acoustic wavefront at a third point on the surface of the solid; and (d) comparing the first and second time to determine the acoustic velocity of the wavefront.

Thus, the present invention solves the problem of inherent inaccuracies in the measurement of acoustic velocities that exist in the prior art.

DESCRIPTION OF THE DRAWINGS

FIG. 3 is a diagram of a first transducer assembly that can be used in the present invention.

FIG. 4 is a diagram of a second transducer assembly that can be used as a middle transducer in the present invention.

DESCRIPTION OF THE PREFERRED EMBODIMENT

In the discussion of the figures, the same numbers will be used throughout to refer to the same or similar components. In addition, the figures may not reflect the exact relative dimensions but are merely illustrative and are meant to be helpful to the explanation of the embodiments of the present invention.

Figure 1A:
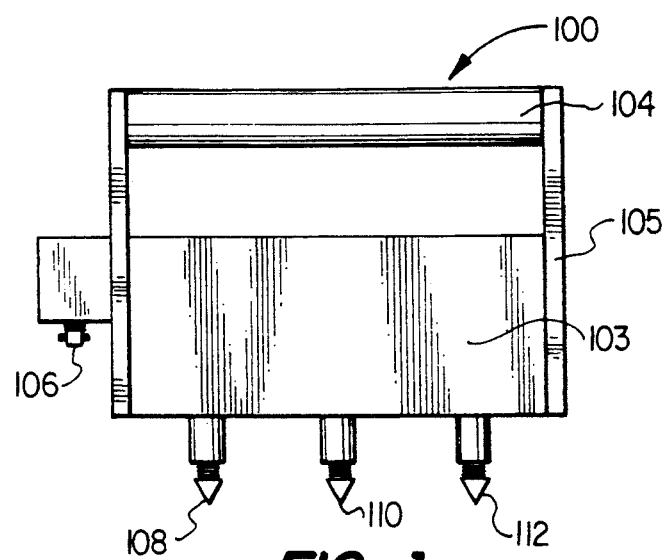
FIGS. 1a and b are two views of a first embodiment of the present invention.
Figure 1B:
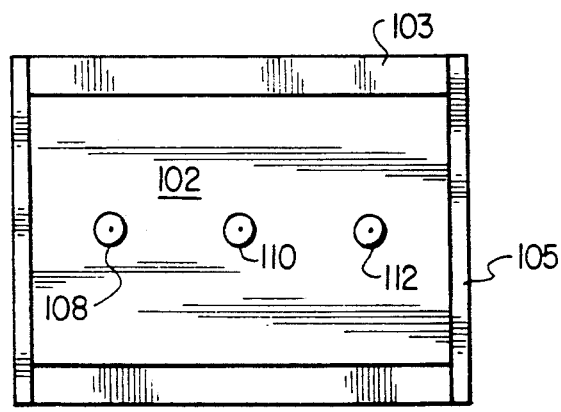
Figure 2:
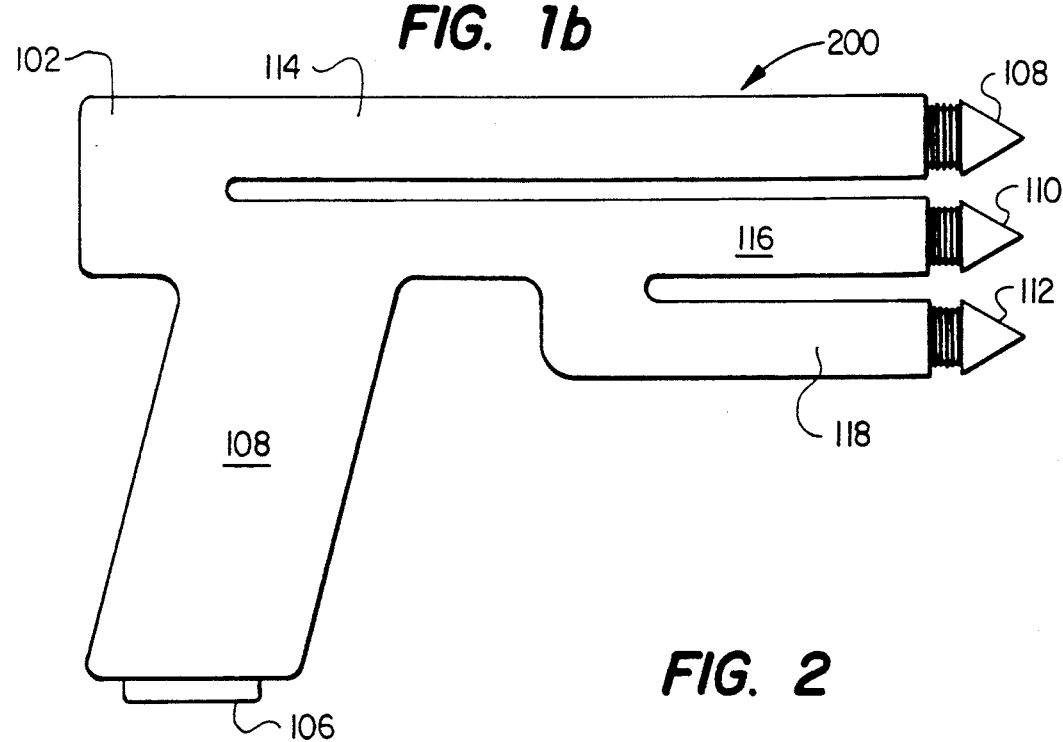
FIG. 2 is a diagram of a second embodiment of the present invention.

FIG. 1(a) shows a side view of first embodiment of the present invention. A device 100 for measuring the velocity of sound in a solid is shown. Device 100 has sides 103 and end plates 105 with a handle 104 which can either be attached to a body 102 as shown in FIG. 1(b) or can be formed as part of a single body as shown in FIG. 2 which is described more in detail below. Body 102 which can be fabricated from any low acoustic dampening material, including but not limited to urethane foam. Sides 103 and end plates 105 can be fabricated from wood or aluminum on other well-known similar-strength materials. Handle 104 provides a suitable means for holding device 100 against the object whose acoustic velocity is to be measured. Attached to body 102 is an input/output connector 106. Such connectors may be either a single or multiple connector or connectors and are well known in the art.

A transmitting transducer assembly 108 is mounted on body 102 and a more detailed description of assembly 108 is provided using FIG. 3 below. Transducer assembly 108 is electrically connected through input-/output connector 106 to a pulse generator (not shown). The pulse generator provides a square wave voltage pulse of suitable amplitude and frequency which causes the piezoelectric crystal in assembly 108 to oscillate. These oscillations are mechanically coupled through assembly 108 to the solid. Thus, assembly 108 is used to transmit acoustic energy to the object.

A first receiving transducer assembly 110 is mounted on body 102 as shown in FIG. 1. The construction of assembly 110 is similar to that of assembly 108 and will be described in more detail below. Assembly 110 is electrically connected through input/output connector 106 to a wave form analysis unit (not shown) which will be discussed further below. Assembly 110 receives acoustic signals transmitted through the object and converts these acoustic signals using a piezoelectric crystal or similar transducing material to generate a first set of electrical pulses.

A second receiving transducer assembly 112 is mounted on body 102 a fixed distance from the first receiving transducer and on an extension of the line passing through the location of assembly 108 and assembly 110. Assembly 112 is electrically connected through the input/output connector 106 to the wave form analysis unit. Assembly 112 contacts the solid and receives acoustic signals transmitted through the solid, converting the acoustic signals through the use of a piezoelectric crystal to a second set of electrical pulses.

The wave form analysis unit (not shown) receives the first and second set of electrical pulses as well as the electrical pulse provided to assembly 108. The wave form analysis unit can be, for example, an oscilloscope, or some other device that allows determination of the time difference between the time of arrival for the first set of electrical pulses and the second set of electrical pulses. The wave form analysis unit may also contain a microprocessor or some other calculational type device which could be used to determine the acoustic velocity or transit time directly. Such methods may include for example, the digitizing of the first and second set of electrical pulses as is well known in the art. After digitizing the pulses, a flip-flop can be used to generate a pulse of constant amplitude having a leading edge corresponding to the leading edge of the first electrical pulse on the first set of electrical pulses and having a trailing edge corresponding to the leading edge of the first pulse of the second set of electrical pulses. A frequency counter in the inverse mode can be used to generate a time which then can be used to quickly calculate the velocity based upon the fixed distance between the first and second receiving transducer assemblies.

The wave form analysis unit may also include an amplifier or amplifiers internal to the wave form analysis unit to improve the signal to noise ratio of the electrical pulses or such amplifiers can be external to the wave form analysis unit. All of the elements for such a wave form analysis unit are well known in the art and are commercially available.

FIG. 2 shows a second embodiment of the present invention. A device 200 for measuring the velocity of sound in a solid is shown. Body 102 is fabricated of a solid piece of material which could be metal or a phenolic or a rigid plastic, and includes a handle 104. Since body 102 is fabricated from a single piece, the acoustic energy transmitted through the body from assembly 108 is positioned a relatively long distance from assemblies 110 and 112 by placing assembly 108 on a long arm 114. This increased distance is long with respect to the distances from assemblies 108, 110 and 112 through the object being measured and therefore acoustic energy transmitted through the body will be received by assemblies at a significantly later time and will not affect the measurement of acoustic velocity in the object. The same method is employed in isolating assembly 110 on arm 116 and assembly 112 on arm 118. Otherwise, the operation of this second embodiment and its construction is similar to that for the embodiment shown in FIG. 1.

FIG. 3 shows a cutaway cross-sectional view of a typical transducer assembly 300 which could be used for assemblies 108, 110 or 112. Assembly 300 is attached to body 102 using anyone of a number of methods which are known in the art. Rod 302 can be connected to body 102 using threads or any number of methods known in the art. Rod 302 is connected to transducer assembly 304 in any one of a number of ways known to those in the art. Transducer assembly 304 is fabricated from a conductive material and can be electrically ground through input/output connector 106. Rod 302 can be fabricated out of a number of materials including both conductive and non-conductive materials. In the case of non-conductive materials, transducer assembly 304 must be electrically connected to body 102 which can be accomplished in various ways including, for example, the placement of a conductive tape on the threads of rod 302 at its connection with assembly 304 and running a wire through a notch in the side of rod 302 to establish electrical connection between transducer assembly 304 and body 102. Transducer assembly 304 can be fastened to rod 302 in any one of a number of ways known in the art.

Rod 302 is connected to transducer assembly 304 in such a manner that a small void is formed. Elastic spacer 306 is placed in this void parallel and adjacent to the flat face of rod 302. Rod 302 and elastic spacer 306 have a hole in the center through which a cable 308 passes through. Cable 308 is electrically connected to a metal disc 310 and is connected through input/output connector 106 to the pulse generator (not shown). Metal disc 310 is parallel and adjacent to elastic spacer 306 parallel to the face of rod 302 but electrically insulated from rod 302. Metal disc 310 is parallel to and in electrical contact with piezoelectric crystal 312. Piezoelectric crystal 312 is a commercially available crystal and can generate either compressional or shear wave acoustic energy. Crystal 312 is provided with a layer of gold on both cylinder faces which allows electrical contact between one face of crystal 312 and metal disc 310 and between the other face of crystal 312 and transducer assembly 304. This allows for a voltage to be impressed across piezoelectric crystal 312 and causing the oscillations of crystal 312 as are well known.

Transducer tip 316 is attached to the end of assembly 304 as shown and is mechanically coupled to crystal 312. Transducer tip 316 can be fabricated in various shapes and various materials based upon the type of solid through which the acoustic velocity is to be measured and the surface up against which the transducer tip 316 is to be placed. For example, against a hard rock, a pointed transducer tip 316 as shown in FIG. 3 fabricated out of tool steel might be appropriate whereas for a softer material a more blunt shape might be more appropriate.

Both the compressional and shear wave crystals 312 could be fitted into a single transducer assembly 304, and through the use of a simple switch, and two conductors similar to wire 308 either the compressional or shear wave piezoelectric crystal 312 could be activated independently.

In order to ensure good contact between assemblies 108, 110 and 112 with a solid whose acoustic velocity is to be measured and whose surface is not flat, a spring-loaded transducer device 400 can be employed for transducer assembly 110. Device 400 is virtually identical to device 300 shown in FIG. 3, however, in device 300, rod 302 was firmly affixed to body 102, while in device 400, rod 302 is fitted into a recess in body 102 and spring loaded by spring 318 such that it makes suitable contact with the surface of the solid whose acoustic velocity is to be measured through tip 316 in spite of any differences in flatness between assemblies 108 and 112.

In operation, acoustic energy is transmitted into the solid at a first point on the surface of the solid through transmitting transducer assembly 108 forming an acoustic wavefront in the solid. The time of arrival of the acoustic wavefront at a second point on the solid is recorded by the waveform analysis unit for through the operation of receiving transducer assembly 110. The time of arrival of the acoustic wavefront at a third point on the solid is recorded by the waveform analysis unit for through the operation of receiving transducer assembly 112. The difference in the two time of arrivals is determined by any means well known in the art. An acoustic velocity of the solid is then determined by dividing the known fixed distance between assemblies 110 and 112 by this time difference by anyone of a number of manual or electronic methods known in the art.

Having thus described the invention by reference to certain of its preferred embodiments, it is respectfully pointed out that the embodiments described are illustrative rather than limiting and that many variations and modifications are possible within the scope of the present invention. Many such variations and modification may appear obvious and desirable to those skilled in the art based upon the foregoing description of preferred embodiments.

Having thus described the invention, we claim:

1. A hand-held portable device for contact measurement of the velocity of sound in a solid comprising:
   (a) a body having a handle;
   (b) a transmitting transducer assembly on the body for converting electrical pulses to a first set of acoustic pulses and transmitting first set of acoustic pulses to the solid;
   (c) a first receiving transducer assembly on the body capable of moving along an axis perpendicular to a line formed between the first receiving transducer assembly and the transmitting transducer assembly a first distance from the transmitting transducer assembly for receiving the first set of acoustic pulses transmitted through the solid and converting the first set of acoustic pulses to a first set of electrical pulses;
   (d) a second receiving transducer on the body a second distance along a line formed by the transmitting transducer assembly and the first receiving transducer, further removed from the transmitting transducer assembly than is the first receiving transducer assembly for receiving the first set of acoustic pulses transmitted through the solid and converting the first set of acoustic pulses to a second set of electrical pulses; and
   thereby enabling measurement of acoustic velocity of the solid by measuring the time of receipt difference between the first and second set of electrical pulses and elimination of the coupling effects on the measurement.

2. The device of claim 1 wherein the transmitting transducer assembly, first receiving transducer assembly, and second receiving transducer assembly are mounted in a straight line.

3. The device of claim 1 wherein the first distance is much less than a path through the body between the transmitting transducer assembly and the receiver transducer assemblies.

4. The device of claim 1 wherein the transmitting and receiving transducer assemblies further comprise piezoelectric crystals.

5. The device of claim 1 wherein the transmitting and receiving transducer assemblies further comprise compression wave generating piezoelectric crystals.

6. The device of claim 1 wherein the transmitting and receiving transducer assemblies further comprise shear wave generating piezoelectric crystals.

7. The device of claim 1 wherein the transmitting and receiving transducer assemblies further comprise shear and compression wave generating piezoelectric crystals.

8. A hand-held portable device for reducing coupling effects in contact measurements of the velocity of sound in a solid comprising:
   (a) a first arm having a lengthwise axis;
   (b) a second arm, shorter than said first arm whose lengthwise axis is substantially parallel to the lengthwise axis of and a first distance from said first arm and connected to said first arm over a small portion of said first arm's length;
   (c) a third arm having a lengthwise axis which is substantially parallel to the lengthwise axis of and substantially the same length as the first arm at substantially the same distance from, in opposite direction and in the same plane as the first arm;

(d) a handle connected to said first and third arms suitable for applying a force along lengthwise axes of said first, second and third arms;

(e) a first transducer assembly rigidly attached at an end of the third arm opposite the handle for transmitting acoustic signals into the solid;

(f) a second transducer assembly rigidly attached at an end of the first arm opposite the handle said first distance being much less than an acoustic path along the lengthwise axis of the third arm through the handle and along the lengthwise axis of the first arm, said second transducer assembly capable of moving along said the lengthwise axis of the first arm for receiving the acoustic signals transmitted into the solid; and (g) a third transducer assembly rigidly attached to the second arm along the lengthwise axis of the second arm, for receiving the acoustic signals transmitted into the solid;

thereby allowing the elimination of the effects of coupling between the first transducer and the solid and allowing discrimination between signals passing through the body of the device and those passing through the solid.

* * * * *